United States Patent
Hiraoka

(10) Patent No.: US 10,188,268 B2
(45) Date of Patent: Jan. 29, 2019

(54) ENDOSCOPE

(71) Applicant: OLYMPUS CORPORATION, Tokyo (JP)

(72) Inventor: Jin Hiraoka, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 18 days.

(21) Appl. No.: 15/416,239

(22) Filed: Jan. 26, 2017

(65) Prior Publication Data

US 2017/0127916 A1    May 11, 2017

Related U.S. Application Data

(63) Continuation of application No. PCT/JP2015/062254, filed on Apr. 22, 2015.

(30) Foreign Application Priority Data

Jul. 28, 2014   (JP) ................. 2014-153104

(51) Int. Cl.
| | |
|---|---|
| *A61B 1/00* | (2006.01) |
| *A61B 1/012* | (2006.01) |
| *A61B 1/018* | (2006.01) |
| *A61B 1/005* | (2006.01) |
| *A61B 8/12* | (2006.01) |

(52) U.S. Cl.
CPC ........ *A61B 1/00098* (2013.01); *A61B 1/0008* (2013.01); *A61B 1/00137* (2013.01); *A61B 1/012* (2013.01); *A61B 1/018* (2013.01); *A61B 8/12* (2013.01)

(58) Field of Classification Search
CPC ............. A61B 1/0008; A61B 1/00089; A61B 1/00098; A61B 1/012; A61B 1/018; A61B 1/0125; A61B 1/00137; A61B 1/005; A61B 1/0051; A61B 1/0052; A61B 1/0053; A61B 1/0055; A61B 1/0056; A61B 1/0057; A61B 1/0058; A61B 2017/00234
USPC ................ 600/107, 123, 153, 154, 127, 129
See application file for complete search history.

(56) References Cited

U.S. PATENT DOCUMENTS

| | | |
|---|---|---|
| 4,245,624 A | 1/1981 | Komiya |
| 5,460,168 A | 10/1995 | Masabuchi et al. |
| 2008/0021269 A1 | 1/2008 | Tinkham et al. |

FOREIGN PATENT DOCUMENTS

| | | |
|---|---|---|
| JP | H02-91504 U | 7/1990 |
| JP | H05-123288 A | 5/1993 |
| JP | 06261857 A | 9/1994 |

(Continued)

OTHER PUBLICATIONS

International Search Report dated Jul. 28, 2015 issued in PCT/JP2015/062254.

(Continued)

*Primary Examiner* — Ryan Henderson
(74) *Attorney, Agent, or Firm* — Scully, Scott, Murphy & Presser, P.C.

(57) ABSTRACT

A treatment instrument lifting adjusting portion including a lifting member and an operation wire is disposed outside of a treatment instrument guiding-out path including an exit member and a tube in a distal end portion. Thus, cleaning work can be performed by inserting, for example, a brush into the treatment instrument guiding-out path, and is easily performed similarly to an endoscope of a type having no treatment instrument lifting function.

1 Claim, 17 Drawing Sheets

(56) References Cited

FOREIGN PATENT DOCUMENTS

JP        10262900  A    10/1998
JP         4199537  B2   12/2008

OTHER PUBLICATIONS

Japanese Office Action dated Jul. 26, 2016 issued in Japanese Patent Application No. 2016-522119.
Extended Supplementary European Search Report dated Jan. 12, 2018 in European Patent Application No. 15 82 7492.8.

ENDOSCOPE

CROSS REFERENCE TO RELATED APPLICATION

This application is a continuation application of PCT/JP2015/062254 filed on Apr. 22, 2015 and claims benefit of Japanese Application No. 2014-153104 filed in Japan on Jul. 28, 2014, the entire contents of which are incorporated herein by this reference.

BACKGROUND OF THE INVENTION

1. Field of the Invention

The present invention relates to an endoscope including a channel that opens at an insertion portion distal end.

2. Description of the Related Art

An endoscope used in a medical field allows, by inserting an elongated insertion portion into a body, observation of an organ in the body, and as necessary, various treatments using a treatment instrument inserted into an insertion channel for the treatment instrument included in the endoscope.

Some endoscopes include a mechanism that can change a protruding direction of the treatment instrument. For example, Japanese Patent No. 4199537 discloses an ultrasound endoscope in which a forceps lifting mechanism can largely change a bent angle of a treatment instrument distal end without contacting with an ultrasound probe.

SUMMARY OF THE INVENTION

An endoscope according to an aspect of the present invention includes an insertion portion configured to be inserted into a subject; a distal end portion disposed at a distal end of the insertion portion and including a housing part having a concave shape and an opening part that opens toward a distal end direction; a tube having a tubular shape disposed in the insertion portion and formed of a flexible material; an exit member fitted to a peripheral edge of the opening part in the housing part of the distal end portion in a liquid-tight manner, including an opening through which the treatment instrument protrudes, and forming a treatment instrument guiding-out path into which the treatment instrument is inserted when the opening is connected so as to communicate with the tube; and an adjusting portion configured to change a protruding direction of the treatment instrument protruding from the opening of the exit member by changing a tilt angle of the treatment instrument guiding-out path within a predetermined range from the opening of the exit member.

DETAILED DESCRIPTION OF THE PREFERRED EMBODIMENT(S)

Embodiments of the present invention will be described below with reference to the accompanying drawings.

(First Embodiment)

Figure 1:
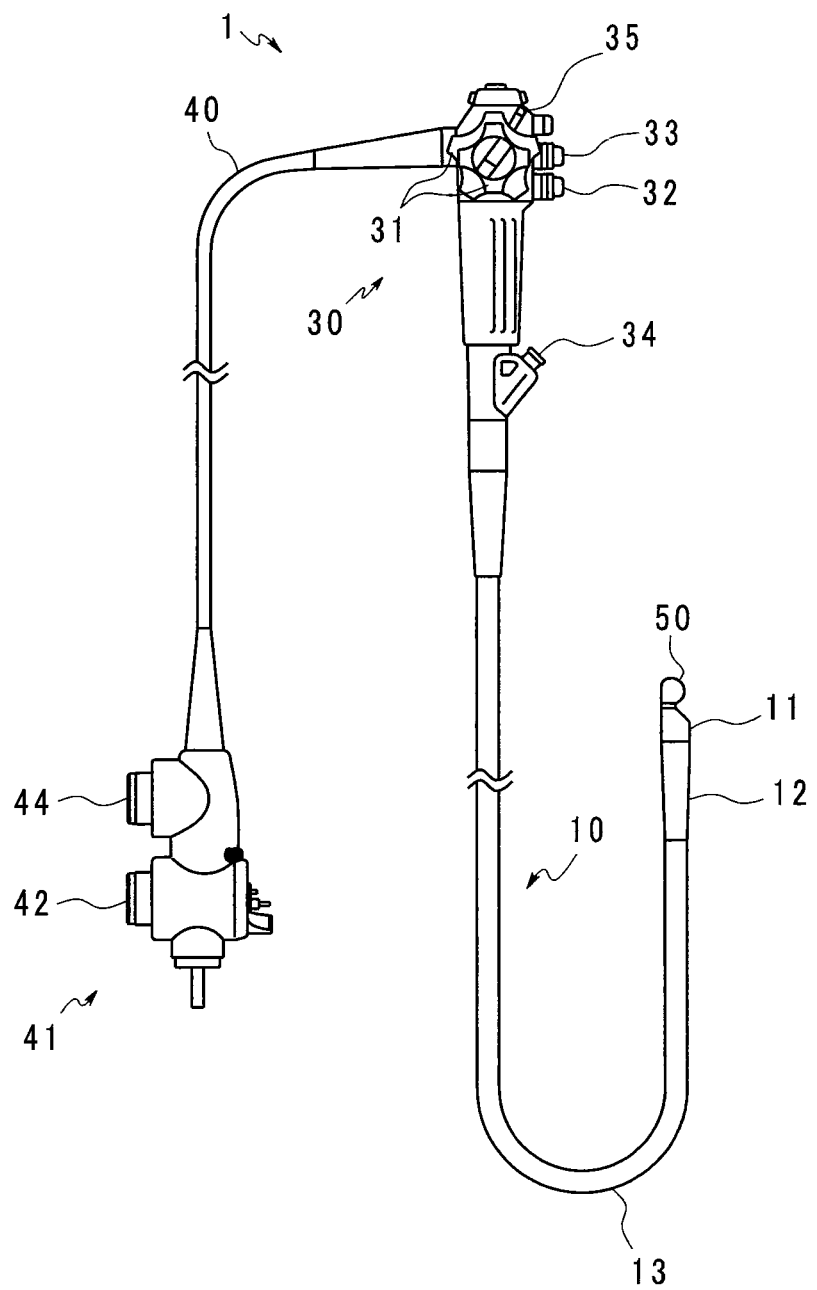
FIG. 1 is an exterior diagram of an ultrasound endoscope according to a first embodiment of the present invention.

In FIG. 1, reference numeral 1 denotes an endoscope to which the present invention is applied. In the present embodiment, the endoscope 1 is an ultrasound endoscope capable of picking up an ultrasound tomographic image of a predetermined observation site in a subject by performing scanning with ultrasound beam in the subject. The endoscope 1 includes an insertion portion 10 that can be inserted into the subject, an operation portion 30 positioned at a proximal end of the insertion portion 10, and a universal cord 40 extending from a side part of the operation portion 30.

The insertion portion 10 is configured to include a distal end portion 11 in which an ultrasound probe portion 50 for picking up an ultrasound tomographic image by transmitting and receiving ultrasound, an image pickup apparatus 15 for picking up an optical image of an object, and an illumination apparatus 16 (refer to FIG. 2) are disposed, a bendable bending portion 12 disposed on a proximal end side of the distal end portion 11, and a flexible tube portion 13 having flexibility that is disposed on the proximal end side of the bending portion 12 and connected with a distal end side of the operation portion 30, the distal end portion 11, the bendable bending portion 12, and the flexible tube portion 13 being provided continuously.

The operation portion 30 is provided with, for example, an angle knob 31 for operating bending of the bending portion 12, an air/water feeding button 32 for performing control of feeding of fluid through the distal end portion 11, a suction button 33 for performing control of suction through the distal end portion 11, and a treatment instrument insertion opening 34. The operation portion 30 is provided with a treatment instrument lifting lever 35 for operating a protruding direction of a treatment instrument protruded from the distal end portion 11 of the insertion portion 10.

An endoscope connector 41 connected with a light source device not illustrated is provided at a proximal end portion of the universal cord 40. Light emitted from the light source device travels through an optical fiber cable inserted into the universal cord 40, the operation portion 30, and the insertion portion 10, and is emitted from the illumination apparatus 16 of the distal end portion 11. Note that the endoscope 1 may be configured to include a light source device such as an LED in the distal end portion 11.

The endoscope connector 41 is provided with a video connector 42 and an ultrasound connector 44. The video connector 42 is detachably connected with a camera control unit that processes an image pickup signal from the image pickup apparatus 15 through a video cable not illustrated and outputs a display signal of an observation image. The ultrasound connector 44 is detachably connected with an ultrasound observation device that drives the ultrasound probe portion 50 through an ultrasound cable not illustrated and processes an observation signal.

The following describes the configuration of the distal end portion 11 of the insertion portion 10 of the endoscope 1.

Figure 2:
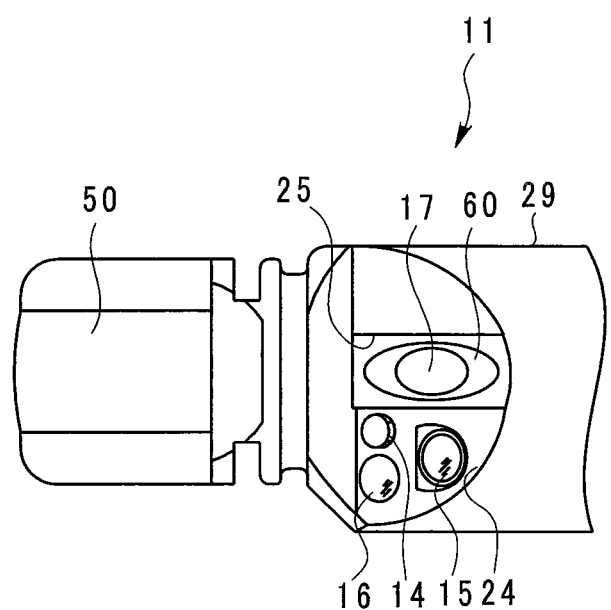
FIG. 2 is a top view of a distal end portion according to the first embodiment of the present invention.

As illustrated in FIG. 2, the distal end portion 11 includes, for example, a distal end rigid portion 29 made of metal or resin. The distal end rigid portion 29 is a substantially shaft-shaped member including, as a central axis, an axis along an insertion direction of the distal end portion 11. The ultrasound probe portion 50 is disposed on the distal end side of the distal end rigid portion 29 so as to protrude toward the distal end direction, and a slant surface portion 24 that is a plane site tilted relative to the central axis is formed on a base part side of the ultrasound probe portion 50.

The slant surface portion 24 is provided to be farther away from the central axis of the distal end rigid portion 29 at a position on the proximal end side of the distal end portion 11 than at a position on the distal end side of the distal end portion 11. In other words, where the slant surface portion 24 is formed, the distal end rigid portion 29 has a larger diameter at a position on the proximal end side of the distal end portion 11 than at a position on the distal end side of the distal end portion 11. The slant surface portion 24 is provided with the image pickup apparatus 15, the illumination apparatus 16, and a fluid feeding portion 14 that is an opening part for performing air/water feeding.

A treatment instrument guiding-out path 17 for causing the treatment instrument to protrude is disposed at the distal end rigid portion 29. The treatment instrument guiding-out path 17 forms a treatment instrument insertion channel disposed from the treatment instrument insertion opening 34 of the operation portion 30 to a concave-shaped housing portion 25 provided to the distal end rigid portion 29. The housing portion 25 is a groove space provided on a side surface part of the distal end rigid portion 29 along the central axis of the distal end rigid portion 29, and forms an opening part that opens toward the distal end direction at the position where the slant surface portion 24 of the distal end rigid portion 29 is formed.

Figure 3:
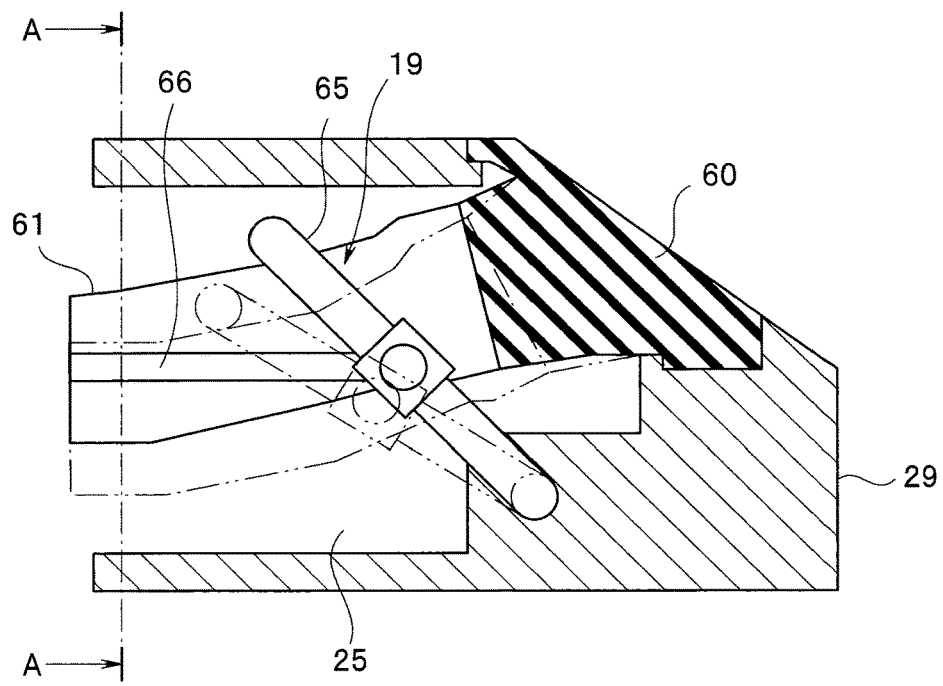
FIG. 3 is an explanatory diagram of a vicinity of a lifting member in the distal end portion according to the first embodiment of the present invention.

A treatment instrument lifting adjusting portion 19 as illustrated in FIG. 3 is provided in the housing portion 25 to change the protruding direction of the treatment instrument protruded from the treatment instrument guiding-out path 17. The adjusting portion 19 changes, along with motion of the treatment instrument lifting lever 35 provided to the operation portion 30, the protruding direction of the treatment instrument protruded from the treatment instrument guiding-out path 17 by changing a tilt angle within a predetermined distance from an opening edge (first end part) on the distal end side of the treatment instrument guiding-out path 17.

Specifically, as illustrated in FIGS. 2 to 5, an exit member 60 including an opening through which the treatment instrument is protruded is attached to a peripheral edge of an opening part in the housing portion 25 of the distal end rigid portion 29. The exit member 60 has an outer peripheral part formed as a liquid-tight portion fitted to the peripheral edge of the opening part of the housing portion 25 in a liquid-tight manner, and in addition, is connected, through a pipe 62, with a tube 61 as a tube member communicated with the treatment instrument insertion opening 34. Thus, the treatment instrument guiding-out path 17 is formed.

The treatment instrument lifting adjusting portion 19 is disposed outside of the tube 61 in the housing portion 25, changes a tilt of an angle variable portion that is a part within a predetermined distance from an opening edge of the exit member 60 by applying a force that causes the tube 61 to bend to an outer surface on the distal end side (exit member 60 side) of the tube 61, so as to change a protruding direction of a treatment instrument JG inserted inside.

Therefore, the tube 61 is formed of a flexible material that is, for example, fluorine resin such as polytetrafluoroethylene (PTFE). The exit member 60 is formed of a soft material such as an elastomer material. Note that the pipe 62 is formed of, for example, a metal material such as stainless steel or a high-strength resin member to efficiently transfer a bending force applied on the tube 61 to the exit member 60.

The adjusting portion 19 is configured to include a lifting member 65 as a transferring portion of which a base part side is rotatably supported by a bottom part of the housing portion 25, of which a distal end side contacts the outer surface of the tube 61, and that transfers an operation force, and an operation wire 66 one end of which is coupled with the lifting member 65. The other end of the operation wire 66 is coupled with the treatment instrument lifting lever 35 of the operation portion 30 through, for example, a link mechanism.

Figure 4:
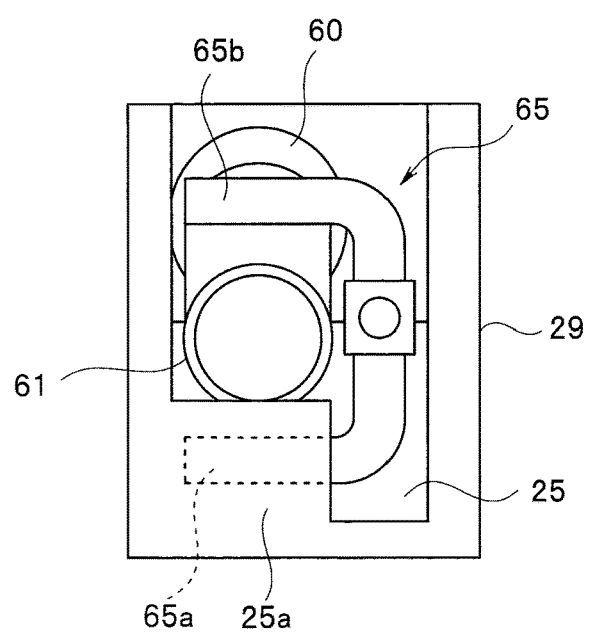
FIG. 4 is a schematic sectional view taken along line A-A in FIG. 3 according to the first embodiment of the present invention.
Figure 5:
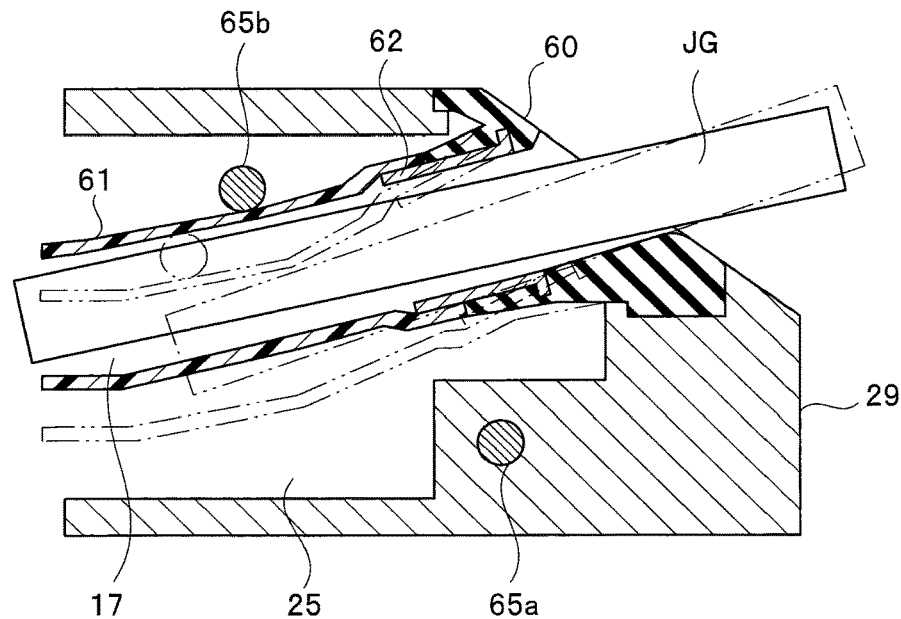
FIG. 5 is an explanatory diagram illustrating a movement of a treatment instrument lifting operation according to the first embodiment of the present invention.

In the present embodiment, as illustrated in FIG. 4, the lifting member 65 is a square C-shaped member having three sides of a rectangle without one vertical side when viewed from an axial direction of the distal end portion 11, and for example, is formed to have two substantially parallel sides by being provided with bending fabrication at two predetermined positions from both ends of a bar member.

One of the two sides of the lifting member 65 that are formed in substantially parallel is a rotation shaft 65a rotatably a bottom part 25a of the housing portion 25, and the other of the two sides is a contact portion 65b in contact with the outer surface of the tube 61. One end of the operation wire 66 is fixed to a part that is a side in the vertical direction of the lifting member 65.

The endoscope 1 having the configuration above can cause the treatment instrument to protrude from a distal end opening part of the treatment instrument guiding-out path 17 by inserting the treatment instrument through the treatment instrument insertion opening 34, thereby introducing the treatment instrument into the subject to perform necessary treatment. Note that, the kind of the treatment instrument is not particularly limited, but is, for example, a puncture needle, biopsy forceps, or a cytodiagnosis brush.

In the treatment, an operator operates the treatment instrument lifting lever 35 provided to the operation portion 30 to change the protruding direction of the treatment instrument. The operation wire 66 is pulled along with the motion of the treatment instrument lifting lever 35, and as illustrated with two-dot chain lines in FIGS. 3 and 5, the lifting member 65 built in the distal end portion 11 rotates about the rotation shaft 65a, and such a force that the contact portion 65b of the lifting member 65 presses the outer surface of the tube 61 to cause bending is transferred.

Accordingly, the tube 61 bends to bow toward an axial center of the distal end portion 11, and the exit member 60 connected with the tube 61 also bows, so that the tilt angle of the treatment instrument guiding-out path 17 changes. As a result, the protruding direction of the treatment instrument JG protruded from the treatment instrument guiding-out path 17 can be changed.

Figure 6:
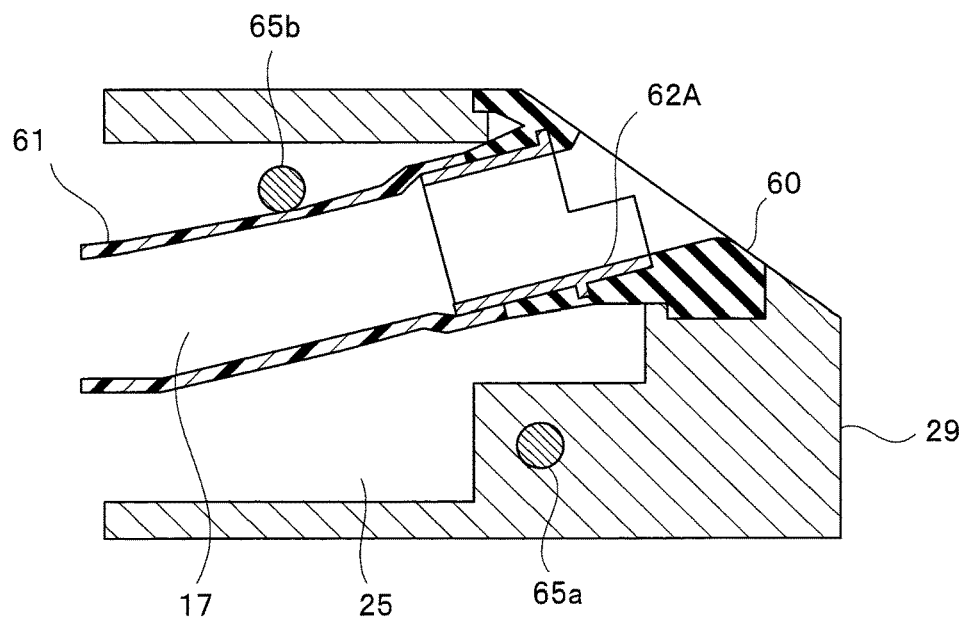
FIG. 6 is an explanatory diagram illustrating a modification of a pipe connecting an exit member and a tube according to the first embodiment of the present invention.
Figure 7:
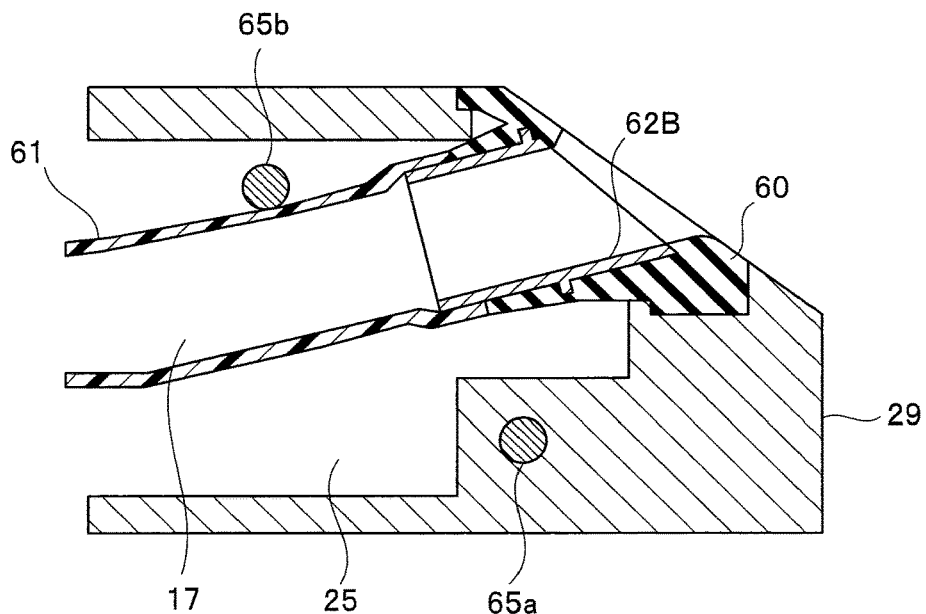
FIG. 7 is an explanatory diagram illustrating another modification of the pipe connecting the exit member and the tube according to the first embodiment of the present invention.

In this case, the treatment instrument guiding-out path 17 is tilted in a predetermined direction relative to a bending direction of the bending portion 12, for example, an up direction. When it is assumed that the treatment instrument guiding-out path 17 is tilted in the up direction, connection between the exit member 60 and the pipe 62 may be such that the treatment instrument guiding-out path 17 is tilted in the up direction in advance by using a pipe 62A of which only a down side is elongated as illustrated in FIG. 6 or a pipe 62B that is obliquely cut to have a longer down side as illustrated in FIG. 7.

Figure 8:
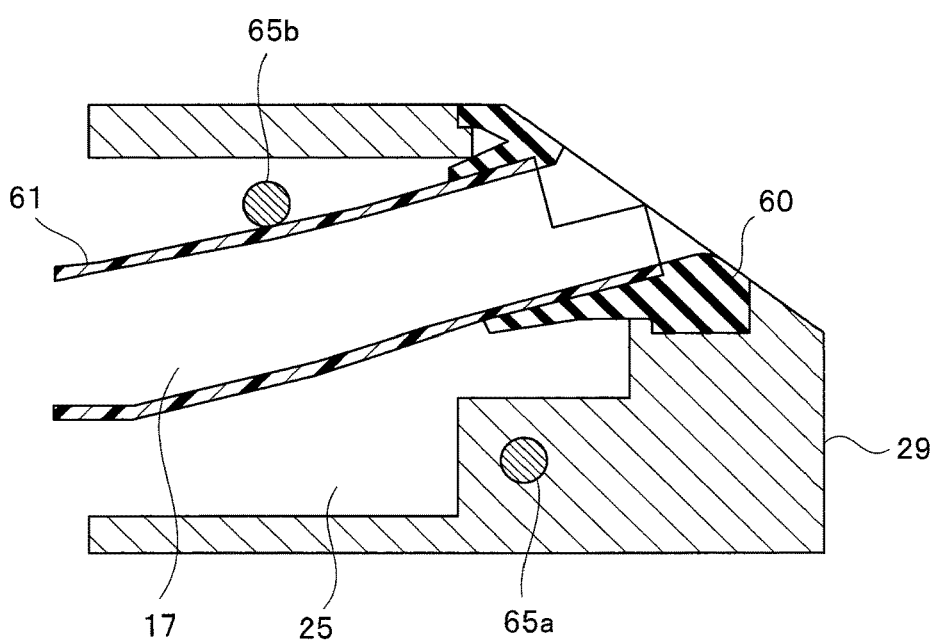
FIG. 8 is an explanatory diagram illustrating an example in which the exit member and the tube are directly connected according to the first embodiment of the present invention.

As illustrated in FIG. 8, the treatment instrument guiding-out path 17 may be tilted in the up direction in advance, by directly connecting the tube 61 and the exit member 60, for example, through integral formation without using the pipe 62. In addition, although not illustrated, the tube 61 may include the pipe 62A of which only a down side is elongated or the pipe 62B that is obliquely cut to have a longer down side so as to tilt the treatment instrument guiding-out path 17 in the up direction in advance.

In this manner, the treatment instrument guiding-out path 17 is tilted to an up side in advance by employing different configurations of connection between the exit member 60 and the tube 61 so that the treatment instrument is guided out while sliding on a down side in the tube 61. In this case, the exit member 60 has a shorter length of an elastomer part on the down side, thereby reducing a slide resistance of the treatment instrument.

After being used, the endoscope 1 is provided with cleaning/disinfecting, and then stored or used again. In the cleaning of the endoscope, cleaning work can be performed easily when cleaning of inside of the treatment instrument guiding-out path 17 is performed.

That is, in the endoscope 1 in the present embodiment, the treatment instrument lifting adjusting portion 19 including the lifting member 65 and the operation wire 66 is disposed outside of the treatment instrument guiding-out path 17 including the exit member 60 and the tube 61 in the distal end portion 11, and thus the cleaning work can be performed by inserting, for example, a brush into the treatment instrument guiding-out path 17, and the cleaning work is easily performed similarly to an endoscope of a type having no treatment instrument lifting function.

Note that the lifting mechanism of the exit member 60 achieved by the lifting member 65 and the operation wire 66 can be applied to the fluid feeding portion 14 for air/water feeding. In addition, in second to sixth embodiments described below, the lifting mechanism of the exit member can be applied to the fluid feeding portion 14 for air/water feeding.

(Second Embodiment)

Figure 9:
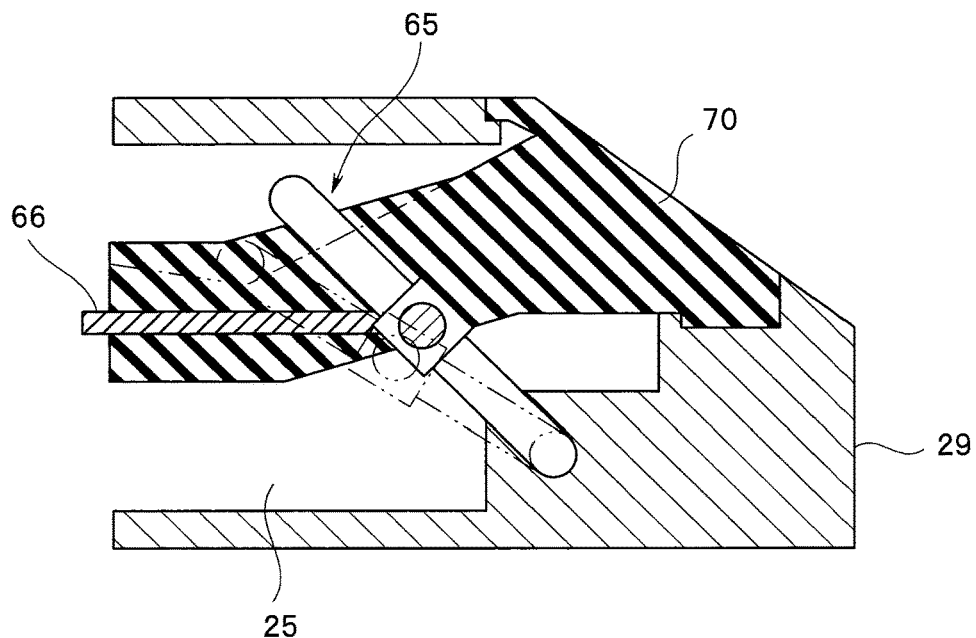
FIG. 9 is an explanatory diagram of the vicinity of the lifting member in the distal end portion according to a second embodiment of the present invention.

The following describes the second embodiment of the present invention. As illustrated in FIG. 9, in the second embodiment, the exit member 60 of the first embodiment is replaced with an exit member 70 elongated to a rear end side, and the contact portion 65b of the lifting member 65 is caused to be in contact with an outer surface on a base part side of the exit member 70. A connection part of the exit member 70 and the tube 61 is moved to the rear end side of the lifting member 65, and the tube 61 is not in contact with the contact portion 65b of the lifting member 65.

Figure 10:
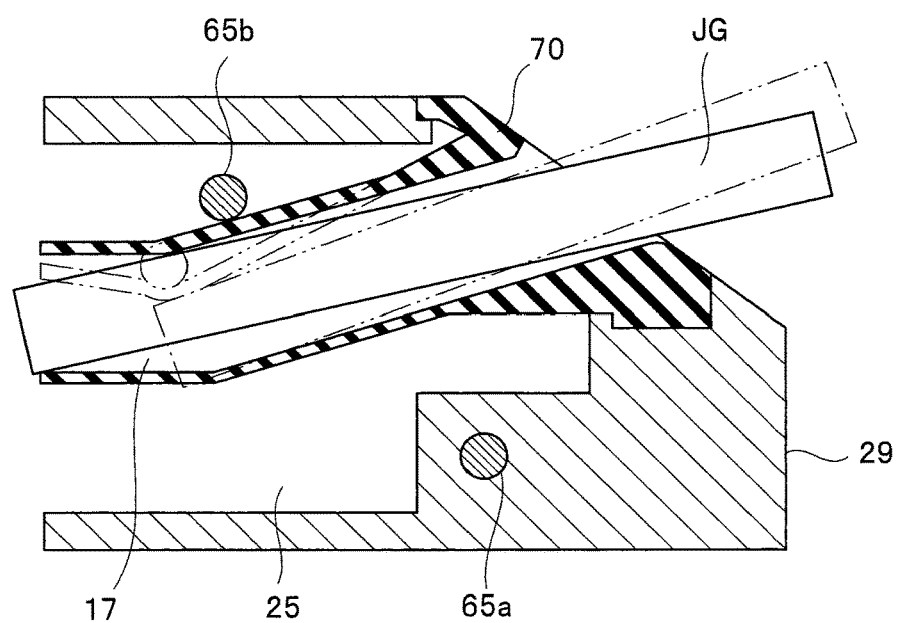
FIG. 10 is an explanatory diagram illustrating the treatment instrument lifting operation according to the second embodiment of the present invention.

In the second embodiment, when the lifting member 65 is rotated by pulling the operation wire 66, a part of the exit member 70 with which the contact portion 65b of the lifting member 65 is in contact deforms as illustrated with two-dot chain lines in FIGS. 9 and 10, thereby enabling a guide-out angle of the treatment instrument JG to be changed. That is, in the second embodiment, a force that changes the tilt angle of the treatment instrument guiding-out path 17 is applied to the exit member 70 instead of being applied to the tube 61 as in the first embodiment.

In the second embodiment, similarly to the first embodiment, for example, a brush can be inserted into the treatment instrument guiding-out path 17 to easily perform cleaning work.

(Third Embodiment)

The following describes the third embodiment of the present invention. Similarly to the first embodiment described above, the third embodiment uses the exit member 60 and the tube 61, but a treatment instrument guiding-out tilt angle is changed by changing a length on a near side of the tube 61 without directly applying, to the exit member 60 and the tube 61, a force that changes the treatment instrument guiding-out tilt angle.

Note that, for this reason, the exit member 60 may be the exit member 70 of the second embodiment, but the following description will be made on an assumption that the exit member 60 and the tube 61 of the first embodiment are used.

Figure 11:
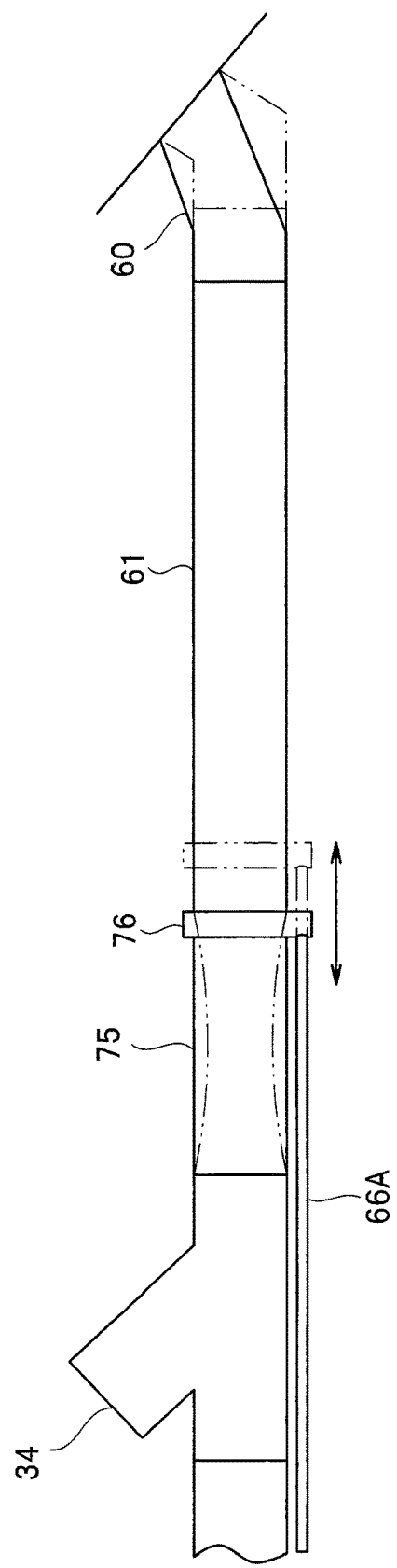
FIG. 11 is an explanatory diagram illustrating a lifting member disposed on a hand side according to a third embodiment of the present invention.

More specifically, as illustrated in FIG. 11, an advancing/retracting portion 75 that is made of a soft material such as an elastomer member and advanceable and retractable in an insertion axial direction by changing a length is provided between a predetermined position on the more distal end side than the treatment instrument insertion opening 34 of the operation portion 30 and a rear end of the tube 61. A ring lifting member 76 is fixed on a rear end side outer periphery of the tube 61 on a front side of the advancing/retracting portion 75, and an operation wire 66A is coupled with the lifting member 76.

The operation wire 66A is formed to have less bow toward the distal end direction and not to impair the flexibility of the insertion portion 10 so as to move the lifting member 76 toward the distal end direction. For example, the operation wire 66A is formed of a wire member having a relatively large diameter or has a configuration in which a wire is inserted into a flexible pipe.

In the third embodiment, the tube 61 is pushed and pulled by moving, forward and backward, the lifting member 76 fixedly provided on the outer periphery of the tube 61, through the operation wire 66A, thereby changing a length of the advancing/retracting portion 75 in the axial direction. This change of the length of the advancing/retracting portion 75 bends the exit member 60 on the distal end side and changes the tilt angle of the treatment instrument guiding-out path 17 as illustrated with a two-dot chain line in FIG. 11.

In the third embodiment, similarly to the first and second embodiments, the cleaning work of the treatment instrument guiding-out path 17 can be easily performed. In addition, in the third embodiment, the configuration of the distal end portion of the endoscope can be further simplified by disposing the lifting member 76 on a hand side, thereby further facilitating reduction of the diameter of the insertion portion.

(Fourth Embodiment)

The following describes the fourth embodiment of the present invention. In the fourth embodiment, the configuration of the lifting member 65 in the first embodiment or the second embodiment described above is changed. The following description will be made on an example in which the lifting member 65 is changed from the second embodiment, but the change may be applied to the first embodiment.

Figure 12:
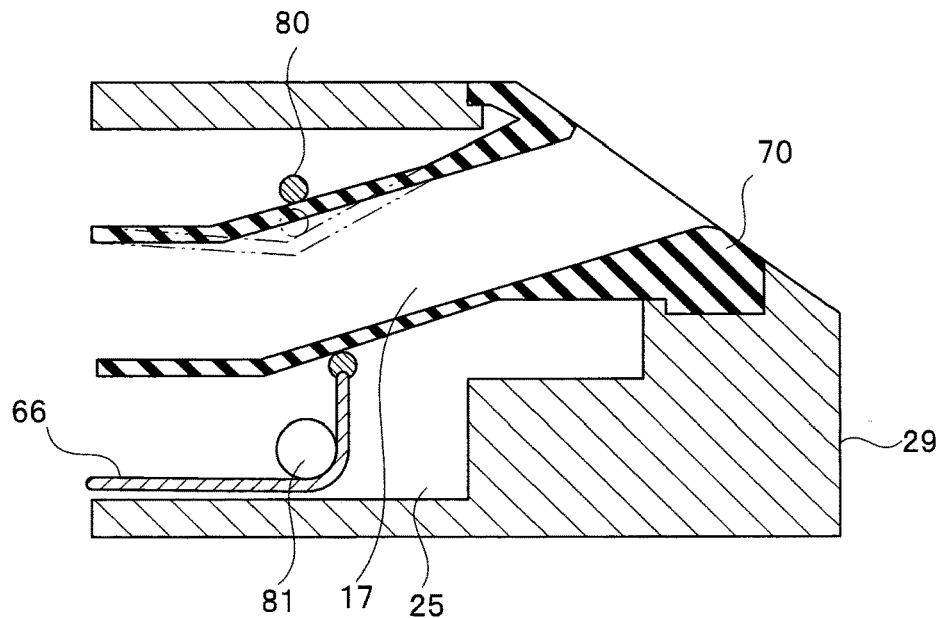
FIG. 12 is an explanatory diagram of the vicinity of the lifting member in the distal end portion according to a fourth embodiment of the present invention.

As illustrated in FIG. 12, a lifting member 80 of the fourth embodiment is formed in a ring shape, and the ring-shaped lifting member 80 is fixed to the outer surface on the base part side of the exit member 70. One end of the operation wire 66 is fixed to a lower end side of the outer periphery of the ring-shaped lifting member 80. The direction of the operation wire 66 from the lifting member 80 is converted from a direction toward the central axis of the distal end rigid portion 29 to the insertion direction by a pulley 81 provided in the distal end rigid portion 29, and the operation wire 66 is coupled with the treatment instrument lifting lever 35 of the operation portion 30.

In this manner, in the fourth embodiment, the operation wire 66 is coupled with, through the pulley 81, the ring-shaped lifting member 80 fixed to the outer surface of base part side of the exit member 70, so that force is applied by the lifting member 80 to press down the base part side of the exit member 70 as illustrated with a two-dot chain line in FIG. 12 when the operation wire 66 is pulled. As a result, the exit member 70 deforms to change the tilt angle of the treatment instrument guiding-out path 17.

In the fourth embodiment, similarly to the embodiments described above, the cleaning work of the treatment instrument guiding-out path 17 can be easily performed.

(Fifth Embodiment)

The following describes the fifth embodiment of the present invention. In the fifth embodiment, the exit member 60 of the first embodiment is changed to a sphere-shaped exit member 85, and the spherical exit member 85 is rotatably mounted on a distal end rigid portion 29A obtained by slightly changing the distal end rigid portion 29 of the first embodiment.

More specifically, the exit member 85 is formed as a sphere including a through-hole 85a which is open at a central part, and the treatment instrument guiding-out path 17 is formed by fitting the pipe 62 to the through-hole 85a of the sphere to connect the tube 61. The lifting member 65 is same as that in the first embodiment, the rotation shaft 65a is rotatably supported by the bottom part 25a of the housing portion 25 of the distal end rigid portion 29, and the contact portion 65b contacts the outer surface of the tube 61.

Note that the lifting member 76 of the third embodiment may be applied as a lifting member that rotates the exit member 85.

A spherical receiving portion 29Aa corresponding to the sphere-shaped exit member 85 is provided to a distal end opening part of the distal end rigid portion 29A, and the exit member 85 is rotatably mounted by covering with a cover 86 while the sphere-shaped exit member 85 being in contact with the receiving portion 29Aa. An assembling property and a rotating property can be achieved by performing this formation so that a center of the exit member 85 matches with a boundary between the distal end rigid portion 29A and the cover 86.

Figure 13:
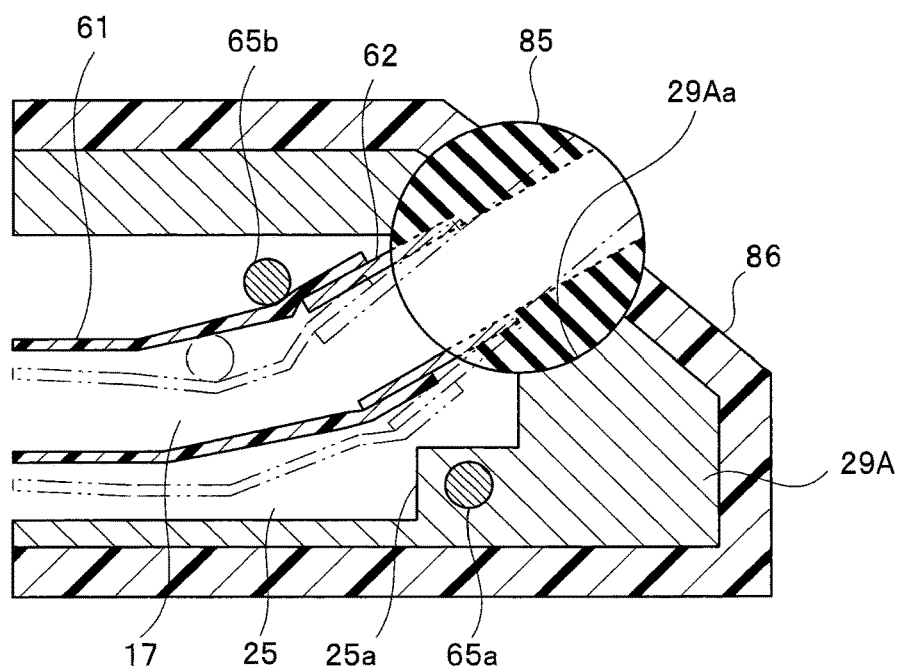
FIG. 13 is an explanatory diagram of the vicinity of the lifting member in the distal end portion according to a fifth embodiment of the present invention.

In the fifth embodiment, the exit member 85 that is a sphere is rotated by rotating the lifting member 65 to bend the tube 61 toward the central axis direction of the distal end rigid portion 29A, thereby changing the tilt angle of the treatment instrument guiding-out path 17 as illustrated with a two-dot chain line in FIG. 13.

The exit member 85 that is a sphere may be formed of, for example, a soft material such as an elastomer member, and the cover 86 may be formed of a rigid member such as plastic to cover the exit member. In contrast, the exit member 85 that is a sphere may be configured with a rigid member such as metal, and the cover 86 may be formed of a soft material such as an elastomer member. In this case, fluid-tightness among the exit member 85, the distal end rigid portion 29A, and the cover 86 is achieved through contact between a soft material such as elastomer and a rigid material such as metal or plastic, and the tilt angle of the treatment instrument guiding-out path 17 is changed by the lifting member 65.

In the fifth embodiment, similarly to the first embodiment, the cleaning work of the treatment instrument guiding-out path 17 can be easily performed.

(Sixth Embodiment)

The following describes the sixth embodiment of the present invention. In the sixth embodiment, the lifting member 65 is changed from the fifth embodiment described above to allow rotation of the exit member 85 that is a sphere in a desired direction.

Figure 14:
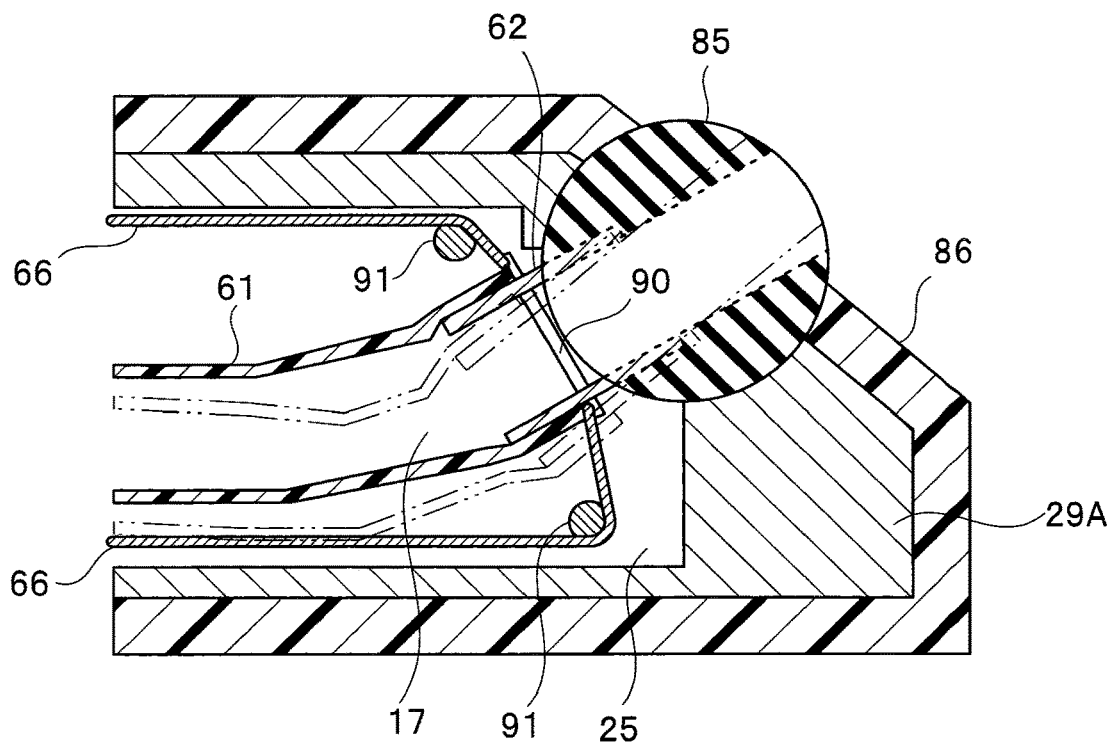
FIG. 14 is an explanatory diagram of the vicinity of the lifting member in the distal end portion according to a sixth embodiment of the present invention.
Figure 15:
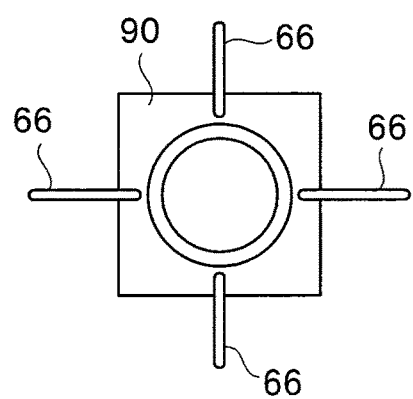
FIG. 15 is an explanatory diagram illustrating a coupling state of an operation wire with the lifting member according to the sixth embodiment of the present invention.

As illustrated in FIG. 14, a lifting member 90 of the sixth embodiment is formed of a rectangular plate member fixed to the pipe 62 fitted to the exit member 85. In the rectangular lifting member 90, for example, as illustrated in FIG. 15, the operation wires 66 are attached to four of up, down, left, and right positions, and each operation wire 66 is extended to the hand side through a pulley 91 and coupled with a wire operation mechanism not illustrated. Note that the distal end rigid portion 29A does not include the bottom part 25a as a bearing of the housing portion 25 along with this change of the lifting member 90.

As the wire operation mechanism, a mechanism similarly to a joystick may be employed to couple the operation wires, or two levers may be coupled with operation wires that operate upward and downward, and leftward and rightward, respectively. Such operation of the wire operation mechanism enables the lifting member 90 to swing and the exit member 85 to rotate to tilt the treatment instrument guiding-out path 17 in an arbitrary direction as illustrated with a two-dot chain line in FIG. 14.

Note that the tilt of the treatment instrument guiding-out path 17 into an arbitrary direction by such a wire operation mechanism may be applied not only to the fifth embodiment described above but also to the ring-shaped lifting member 80 of the fourth embodiment. That is, such a structure may be applicable that wires may be attached to four positions in up, down, left, and right directions of the ring-shaped lifting member 80, and a direction of each wire is changed through a pulley.

In the sixth embodiment, similarly to the first embodiment, the cleaning work of the treatment instrument guiding-out path 17 can be easily performed. However, the sixth embodiment additionally has an advantage that, since the treatment instrument guiding-out path 17 can be caused to face to a direction other than the up and down directions, for example, when a puncture needle is protruded through the treatment instrument guiding-out path 17, such adjustment is possible to easily move the puncture needle into the scanning surface even if the puncture needle is to be off an ultrasound scanning surface.

(Seventh Embodiment)

Figure 16:
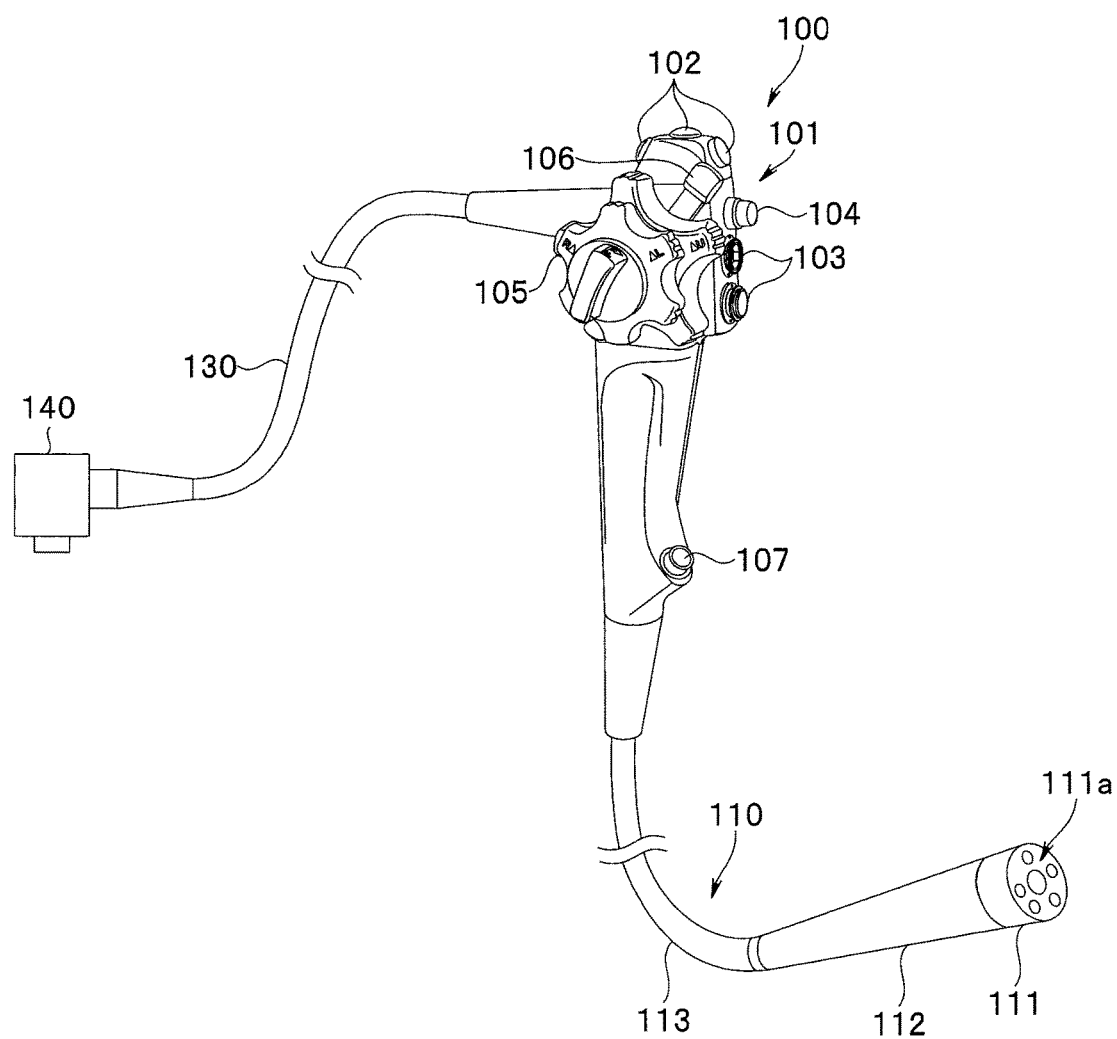
FIG. 16 is an exterior diagram of an optical endoscope according to a seventh embodiment of the present invention.

The following describes the seventh embodiment of the present invention. The seventh embodiment is applied to an optical endoscope that optically observes an object. As illustrated in FIG. 16, an endoscope 100 in the seventh embodiment includes an operation portion 101, an insertion portion 110, a universal cord 130, and an endoscope connector 140, and is connected, through the endoscope connector 140, with peripheral devices, not illustrated, such as a light source device, a signal processing device, and an air/water feeding device.

Operation members such as a video switch 102, an air/water feeding operation button 103, a suction operation button 104, and a bending operation knob 105 are disposed in the operation portion 101, and in addition, a nozzle lifting lever 106 to be described later is disposed in the operation portion 101. A treatment instrument insertion opening 107 is disposed on the more distal end side than these operation members.

The insertion portion 110 is configured with a distal end portion 111, a bending portion 112, and a flexible tube portion 113. The bending portion 112 is bent by the bending operation knob 105 provided to the operation portion 101, and is disposed between the distal end portion 111 and the flexible tube portion 113.

Figure 17:
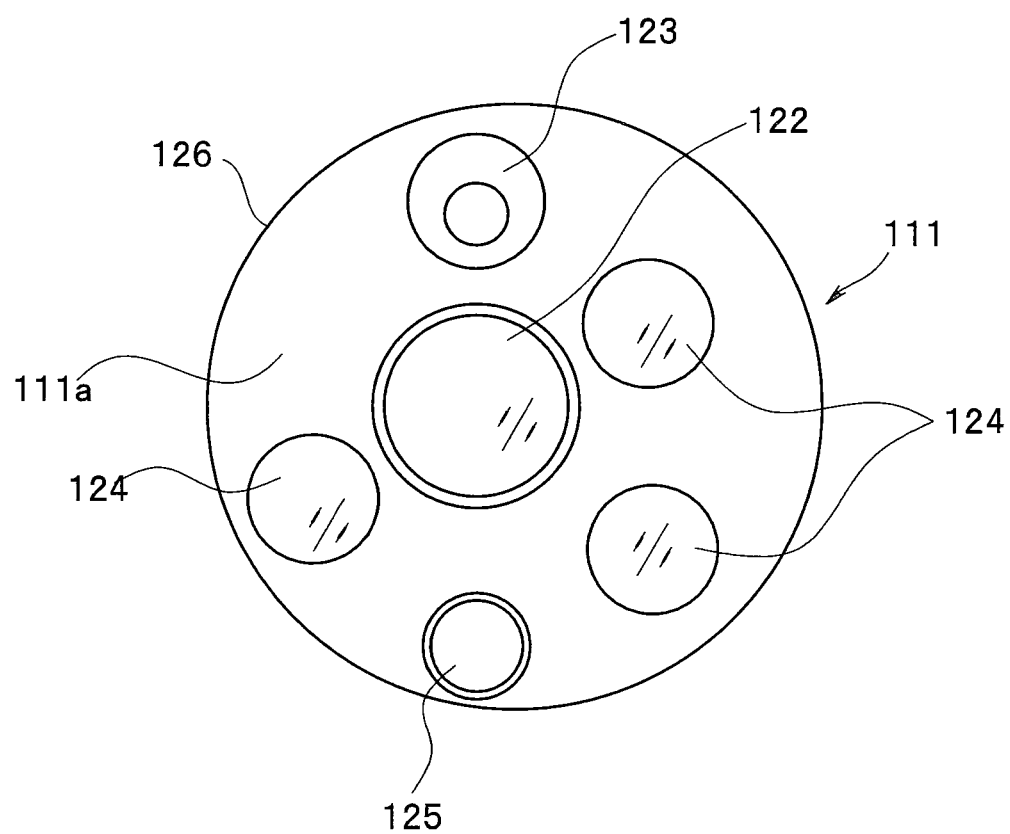
FIG. 17 is a front view of the distal end portion according to the seventh embodiment of the present invention.

As illustrated in FIG. 17, an object lens 122 positioned on a distal end side in an optical axis direction of an object optical system not illustrated is disposed on a distal end surface 111a on an insertion-directional distal end side (hereinafter simply referred to as a distal end side) of the distal end portion 111. An exit member 123 configured as a nozzle capable of cleaning a surface of the object lens 122 by ejecting fluid such as water or air, three illumination windows 124, and a distal end opening 125 of a suction tube path serving as the treatment instrument guiding-out path, for example, are disposed on the distal end surface 111a.

Note that the object lens 122, the exit member 123, the illumination windows 124, and the distal end opening 125 are provided to a distal end rigid portion 126 that is a frame configuring the distal end portion 111.

Gas or liquid is selectively discharged from the exit member 123 by a button operation of the air/water feeding operation button 103 of the operation portion 101. Mucus in a body cavity and contamination removed from the surface of the object lens 122 by fluid from the exit member 123 are recovered from the distal end opening 125 of the suction tube path serving as the treatment instrument guiding-out path, through the suction tube path provided from the treatment instrument insertion opening 107 to the distal end opening 125 in the insertion portion 110 by a button operation of the suction operation button 104 of the operation portion 101.

The exit member 123 in the seventh embodiment serves as a Direction-variable nozzle that can change a fluid discharge direction in accordance with an operation of the nozzle lifting lever 106, not as a nozzle having a fixed structure in which a fluid discharge opening is disposed toward the object lens 122 as conventionally done. Such a nozzle may be the lifting members 65, 76, 80, and 90 that change the tilt angle of the treatment instrument guiding-out path 17 of the first to sixth embodiments described above, but is the exit member 123 as illustrated in FIG. 18 in the seventh embodiment.

Figure 18:
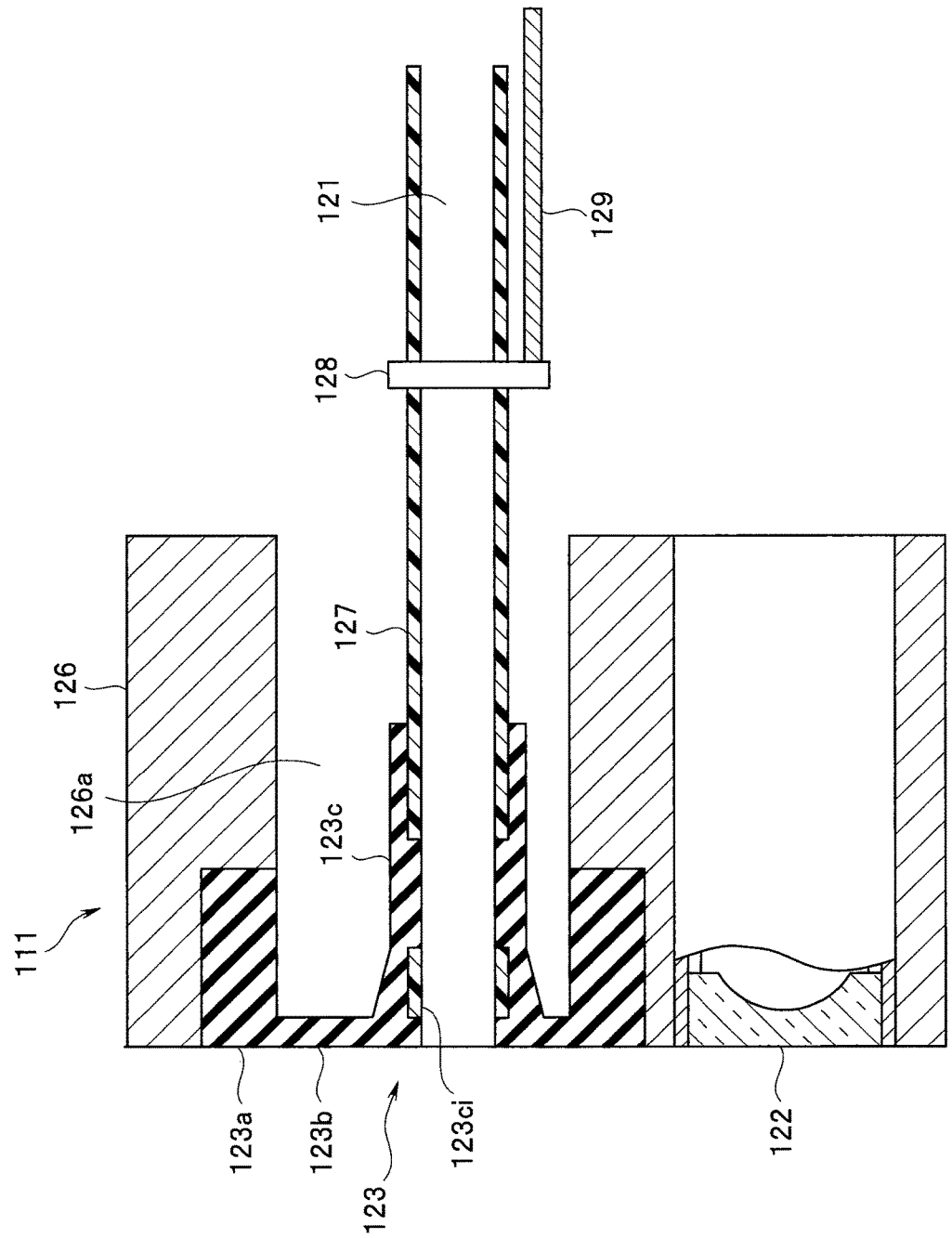
FIG. 18 is an explanatory diagram of the vicinity of the lifting member in the distal end portion according to the seventh embodiment of the present invention.

More specifically, as illustrated in FIG. 18, in the distal end rigid portion 126, a housing portion 126a housing the exit member 123 is provided adjacent to the object lens 122, and the exit member 123 is attached to the housing portion 126a. The exit member 123 is configured to include a cylindrical mounting portion 123a attached to a distal end opening part of the housing portion 126a in a liquid-tight manner, a thin-wall distal end surface portion 123b that forms a distal end surface of the mounting portion 123a and on which a fluid discharge opening is open, and a cylindrical connection portion 123c protruding into the housing portion 126a from a back surface side of the distal end surface portion 123b. The connection portion 123c of the exit member 123 is connected with a tube 127 to become an air/water feeding tube path 121 that forms an air/water feeding channel.

The exit member 123 having such a configuration is formed of a material such as rubber that is more flexible than a material of the tube 127 forming the air/water feeding tube path, and the thin-wall distal end surface portion 123b is configured to be deformable. In the exit member 123, a partial site 123ci that forms a discharge opening near an opening part of the distal end surface portion 123b on the distal end side of the connection portion 123c is formed more rigid than on the hand side so as to be hardly deformed.

Note that a discharge opening part of the exit member 123 is provided being decentered toward the object lens 122 with respect to the center of the mounting portion 123a.

The tube 127 forming the air/water feeding tube path is configured with a material that can transfer a force in the axial direction but only has flexibility enough to allow bending, for example, fluorine resin such as polytetrafluoroethylene (PTFE). A ring-shaped lifting member 128 is fixed to an outer periphery part on the hand side of the tube 127, and is coupled with one end of an operation wire 129. The other end of the operation wire 129 is coupled with the nozzle lifting lever 106 on the hand side.

The lifting member 128 and the operation wire 129 are same as the lifting member 76 and the operation wire 66A described in the third embodiment above, and are configured to cause the discharge opening of the exit member 123 to lift by bending the tube 127 itself by pushing the tube in the axial direction so as to change the fluid discharge direction.

Figure 19:
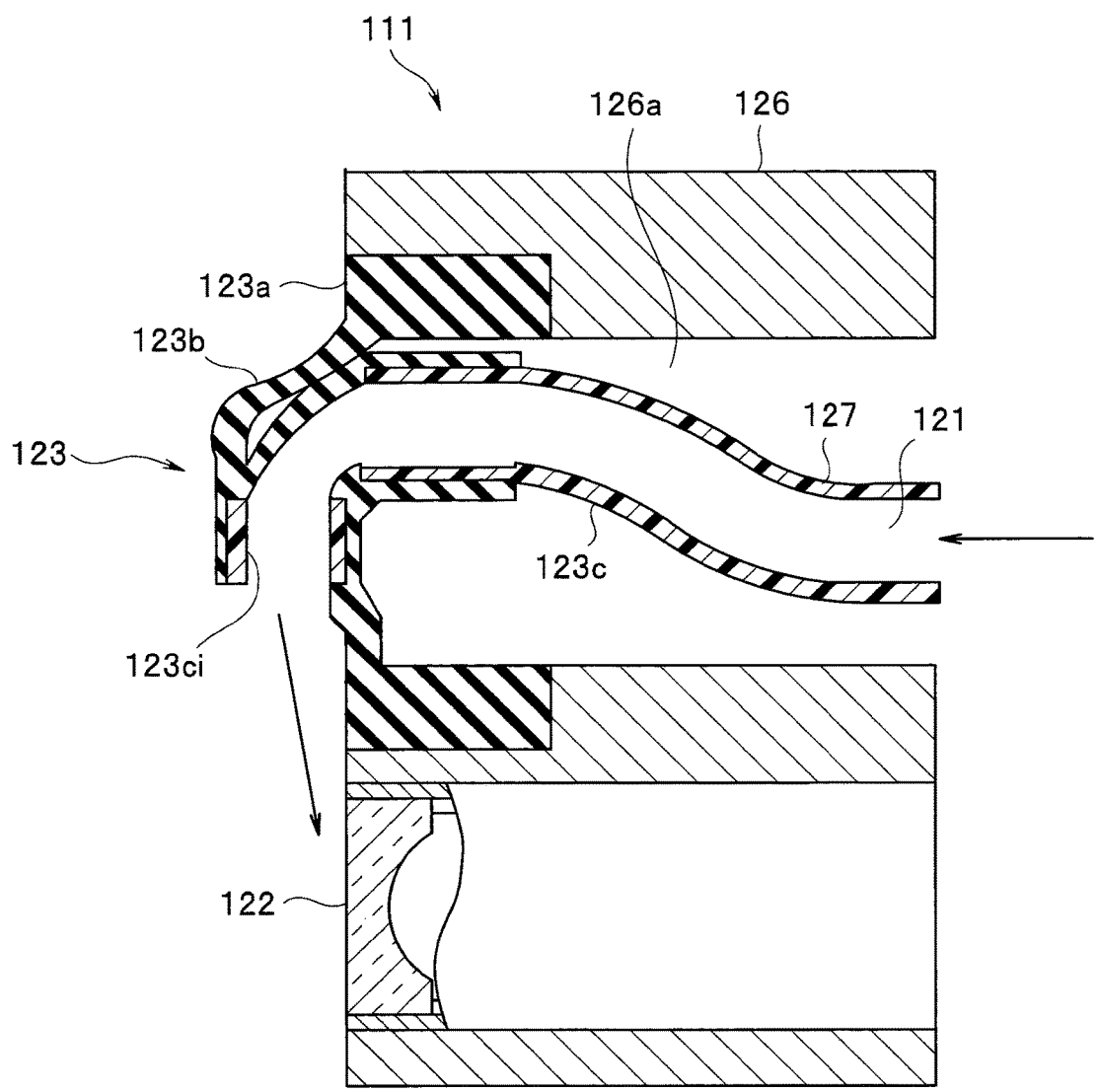
FIG. 19 is an explanatory diagram illustrating a state in which the exit member is lifted according to the seventh embodiment of the present invention.

As illustrated in FIG. 18, when the discharge opening of the exit member 123 faces toward the axial direction, if the tube 127 is pushed forward through the operation wire 129 and the lifting member 128, the thin-wall distal end surface portion 123b and a flexible portion of the connection portion 123c deform as illustrated in FIG. 19, and the discharge opening of the exit member 123 deforms to face a distal end surface of the object lens 122.

That is, the discharge opening part of the exit member 123 decenters toward the object lens 122 with respect to the center of the mounting portion 123a, and thus the deformation is small in a narrow part of the thin-wall distal end surface portion 123b, and with this part as a pivot, a rigid portion part of the discharge opening on the distal end side deforms to lift. Accordingly, fluid such as water is discharged onto the surface of the object lens 122 from the exit member 123 to wash to remove an object attached to the surface of the object lens 122.

The seventh embodiment achieves an effect that, typically, the discharge opening of the exit member 123 opens straight at a distal end, which allows, for example, brushing to facilitate cleaning.

(Eighth Embodiment)

The following describes the eighth embodiment of the present invention. In the eighth embodiment, the lifting member 128 that changes a discharge direction of the exit member 123 is changed from the seventh embodiment. Note that the housing portion 12a of the distal end rigid portion 126 is slightly changed along with this change of the lifting member 128 so as to obtain a distal end rigid portion 126A and a housing portion 126Aa.

Figure 20:
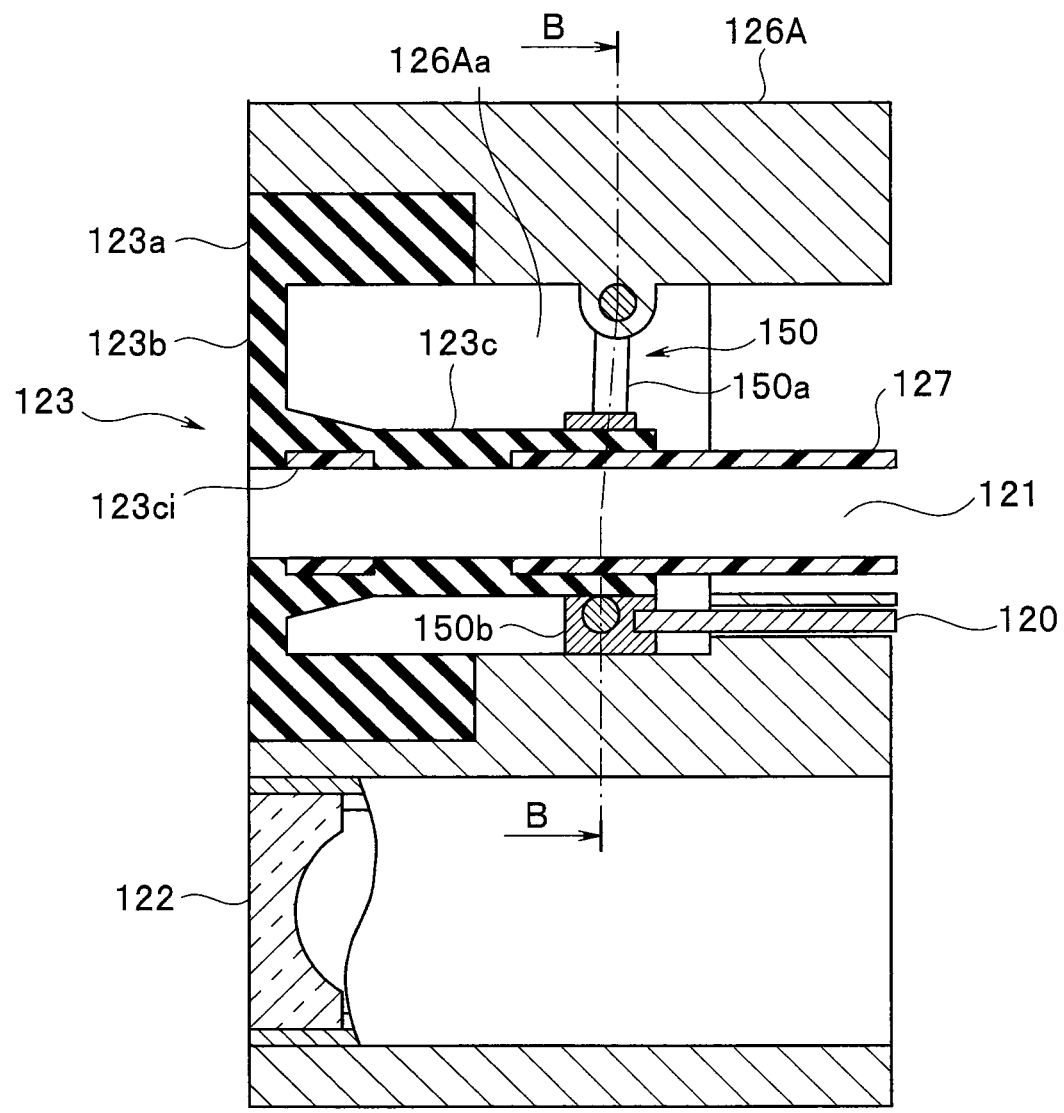
FIG. 20 is an explanatory diagram of the vicinity of the lifting member in the distal end portion according to an eighth embodiment of the present invention.
Figure 21:
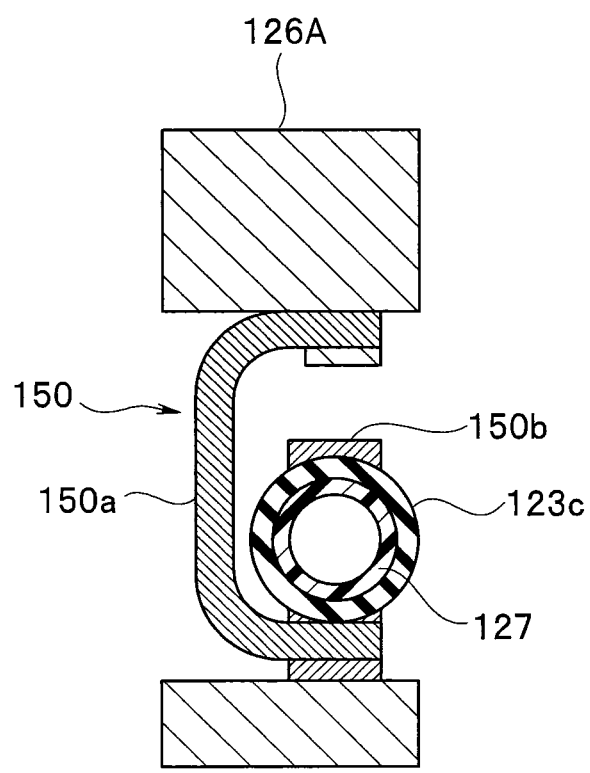
FIG. 21 is a schematic sectional view taken along line B-B in FIG. 20 according to the eighth embodiment of the present invention.

As illustrated in FIGS. 20 and 21, a lifting member 150 of the eighth embodiment is configured to include a C-shaped lever 150a having three sides of a rectangle without one vertical side when viewed from the distal end side, and a lever bearing 150b fixed to a rear-end outer periphery of the connection portion 123c of the exit member 123 connected with the tube 127.

One of two sides of the lever 150a formed substantially in parallel to each other is rotatably attached to a hole provided in an inner surface of the housing portion 126Aa of the distal end rigid portion 126A, and the other of the two side is rotatably supported by a hole provided on an object lens 122 side of the lever bearing 150b. An operation wire 120 is fixed on the hand side of the lever bearing 150b, and coupled with the nozzle lifting lever 106 on the hand side through a path in the distal end rigid portion 126.

Figure 22:
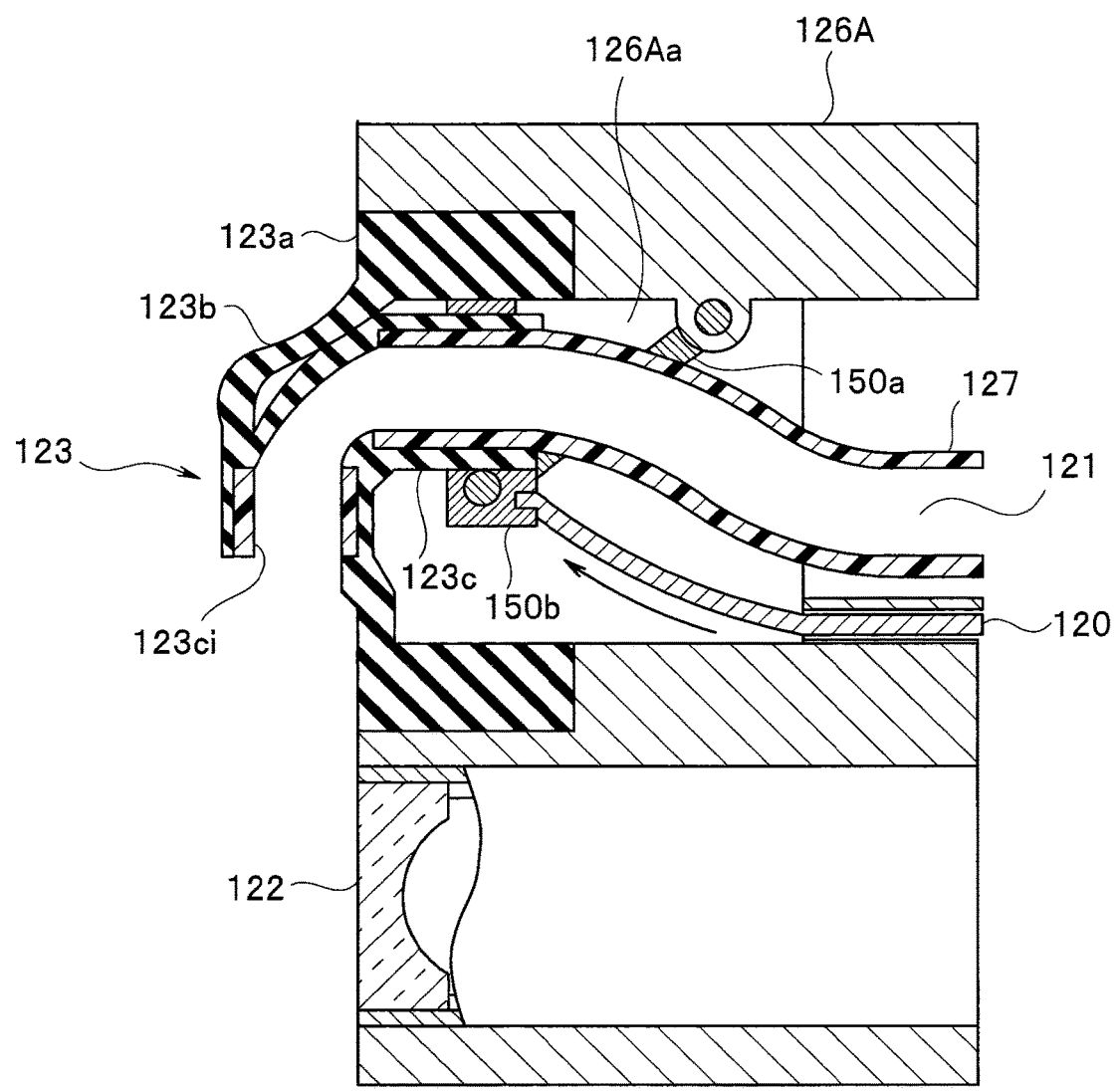
FIG. 22 is an explanatory diagram illustrating a state in which the exit member is lifted according to the eighth embodiment of the present invention.

In the lifting member 150 configured as described above, when the operation wire 120 is pushed forward by an operation of the nozzle lifting lever 106, the lever 150a rotates as illustrated in FIG. 22, and a distal end of the tube 127 moves obliquely forward through the lever bearing 150b. In this case, with the object lens 122 side as a pivot, the thin-wall distal end surface portion 123b of the exit member 123 deforms and the rigid portion part on the distal end side of the discharge opening of the exit member 123 lifts, so that the discharge opening faces toward the distal end surface of the object lens 122.

Similarly to the seventh embodiment, the eighth embodiment achieves an effect that, typically, the discharge opening of the exit member 123 opens straight at the distal end, which allows, for example, brushing to facilitate cleaning.

Figure 23:
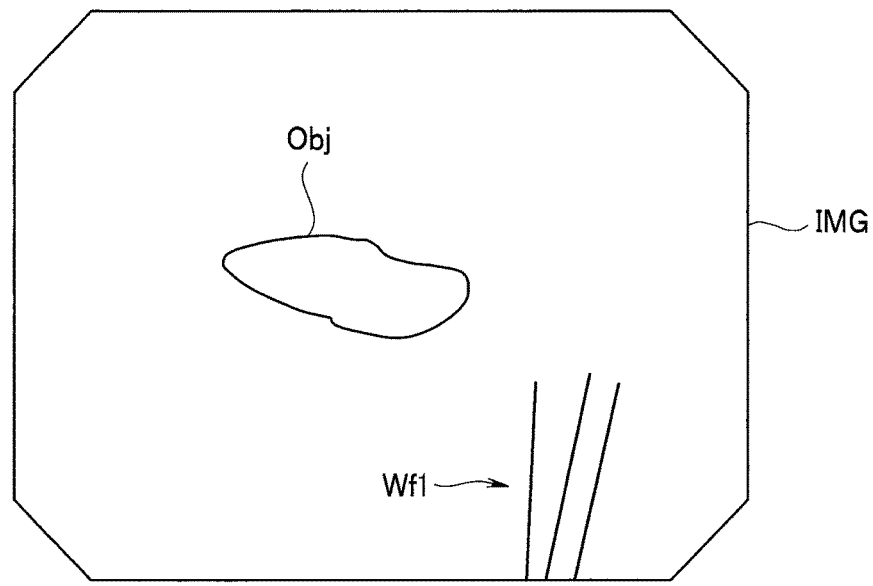
FIG. 23 is an explanatory diagram illustrating an endoscope screen when a cleaning target and a water feeding direction are shifted from each other.

Note that, as illustrated in, for example, FIG. 23, when an object Obj to be cleaned exists on a left side on an endoscope screen, and a direction of water flow Wf1 discharged from the nozzle is not toward the object Obj, the entire distal end portion of the endoscope conventionally needs to be adjusted to face toward a direction in which cleaning needs to be performed. However, this adjustment is potentially unsuccessful, losing view of the object Obj.

Figure 24:
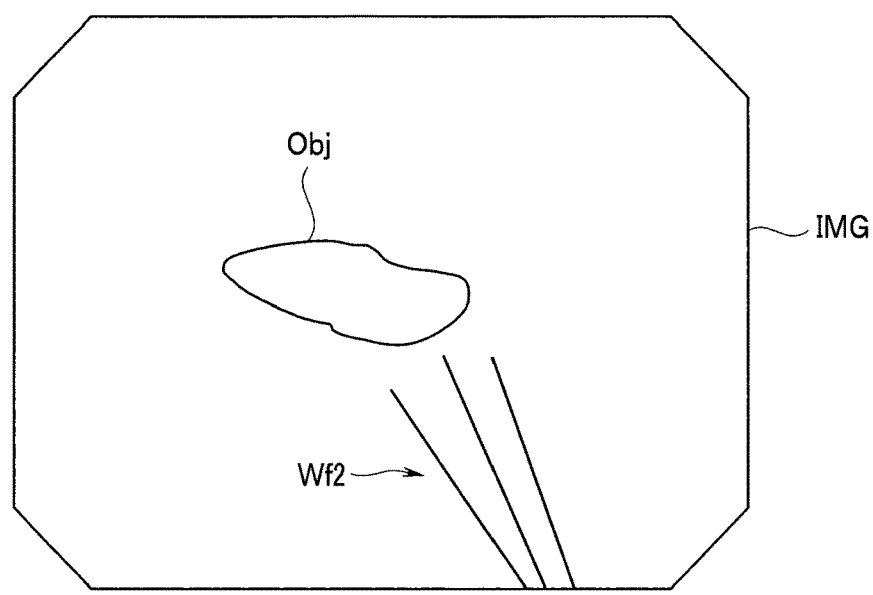
FIG. 24 is an explanatory diagram illustrating the endoscope screen after the water feeding direction is finely adjusted.

On the other hand, a discharge direction of water can be adjusted to achieve water flow Wf2 facing toward the direction of the object Obj to be cleaned as illustrated in FIG. 24 by applying the lifting members 65, 76, 80, 90, 128, and 150 of the first to eighth embodiments above to configure the direction of the nozzle to change in the up and down directions and the left and right directions, thereby reliably performing cleaning without losing view of a target to be cleaned.

What is claimed is:

1. An endoscope comprising:
    an insertion portion configured to be inserted into a subject;
    a distal end portion disposed at a distal end of the insertion portion and including a housing part having a recess and an opening part that opens toward a distal end direction;
    a tube having a tubular shape disposed in the insertion portion and formed of a flexible material;
    an exit member fitted to a peripheral edge of the opening part in a liquid-tight manner in the housing part of the distal end portion, including an opening through which a treatment instrument protrudes, and forming a treatment instrument guiding-out path into which the treatment instrument is inserted when the opening is connected so as to communicate with the tube; and
    an adjusting portion configured to change a protruding direction of the treatment instrument protruding from the opening of the exit member by changing a tilt angle of the treatment instrument guiding-out path by bending the tube connected to the opening of the exit member
    wherein the adjusting portion comprises: a transferring portion made of a bar member, the bar member including a rotation shaft rotatable supported in the distal end portion and a contact portion that is in contact with an outer surface of the tube; and
    an operation wire one end of which is connected between the rotation shaft and the contact portion of the bar member, the operation wire being configured to rotate the transferring portion by another end of the operation wire being moved forward and backward, to bend the tube and change the tilt angle of the treatment instrument guiding-out path.

* * * * *